US00PP34956P3

(12) United States Plant Patent
Perrault et al.

(10) Patent No.: US PP34,956 P3
(45) Date of Patent: Jan. 31, 2023

(54) HOP PLANT NAMED 'HBC 1019'

(50) Latin Name: *Humulus lupulus*
Varietal Denomination: HBC 1019

(71) Applicant: HOP BREEDING COMPANY, L.L.C., Yakima, WA (US)

(72) Inventors: Jason Perrault, Toppenish, WA (US); Michael D. Ferguson, Yakima, WA (US); Scott Varnum, Ellensburg, WA (US); Jaime Avalos P., Granger, WA (US); Scott Herzog, Yakima, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 17/300,967

(22) Filed: Dec. 30, 2021

(65) Prior Publication Data

US 2022/0217883 P1 Jul. 7, 2022

Related U.S. Application Data

(60) Provisional application No. 63/205,709, filed on Dec. 30, 2020.

(51) Int. Cl.
*A01H 6/00* (2018.01)
*A01H 5/12* (2018.01)
*A01H 5/02* (2018.01)

(52) U.S. Cl.
USPC ..... Plt./236
CPC ..... *A01H 6/00* (2018.05); *A01H 5/02* (2013.01)

(58) Field of Classification Search
USPC ..... Plt./236
See application file for complete search history.

*Primary Examiner* — Annette H Para
(74) *Attorney, Agent, or Firm* — Svendsen Legal, LLC

(57) ABSTRACT

A new hop plant named 'HBC 1019' is disclosed. 'HBC 1019' is used for its exceptional and unique aromatic qualities, and is suitable for beer flavoring.

6 Drawing Sheets

Genus and species: *Humulus lupulus*.
Variety denomination: 'HBC 1019'.

STATEMENT REGARDING FEDERALLY SPONSORED RESEARCH OR DEVELOPMENT

None

BACKGROUND OF THE INVENTION

'HBC 1019' is a product of a controlled breeding program carried out by the co-inventors in the Yakima Valley of Washington State. 'HBC 1019' was one of several seedlings resulting from a controlled cross made in 2016 with female parent 'HBC 476' an unpatented variety, and male pollen parent 'ZRCBM'. 'ZRCBM' is a pollen bulk of a multiple of male hop plants, selected for desirable traits including elevated alpha acids, strong vigor, and high pollen shed. Seedling plants from this cross were planted in 2017 and screened for disease resistance and sex in a greenhouse and field nursery near Granger, Wash. A single plant of 'HBC 1019' was selected in 2017. In 2018, 'HBC 1019' was asexually reproduced and expanded to a seven hill plot. In 2019, 'HBC 1019' was asexually reproduced via softwood cuttings near Granger, Wash., and expanded to thirty plants in an evaluation block near Toppenish, Wash. In 2020 'HBC 1019' was further expanded to a two-acre test block near Toppenish, Wash., again with plants asexually reproduced via softwood cuttings. The 'HBC 1019' plants have now been observed and evaluated for several years. Throughout several generations of asexual propagation, 'HBC 1019' has been observed to retain its distinctive characteristics and remain true to type.

SUMMARY OF THE INVENTION

A new and distinct hop plant is described herein, with the 'HBC 1019' cultivar characterized by having cones with high alpha acid and high beta acid content. The new cultivar exhibits sweet fruit, cream caramel, citrus, and floral aromas. The new cultivar is suitable for beer flavoring.

COMPARISON OF 'HBC 1019' TO PARENT PLANT AND COMPARISON CULTIVAR

Table 1. below, sets forth some of the distinguishing characteristics of 'HBC 1019' as compared to its female parent 'HBC 476', and to the 'Chinook' cultivar as a closely comparable cultivar.

TABLE 1

| | INSTANT CV. 'HBC 1019' | FEMALE PARENT 'BC 476' | COMPARISON CV. 'CHINOOK' |
|---|---|---|---|
| Alpha (% of cone weight) | 11.4 | 8.4 | 11.5-15 |
| Beta (% of cone weight) | 8.8 | 5.9 | 3.0-4.0 |
| Co-humulone (% of alpha acids) | 23.0 | 24.4 | 27-31 |
| Total Oil (mL/100 g) | 1.8 | 1.8 | 1.0-2.5 |

BRIEF DESCRIPTION OF THE PHOTOGRAPHS

Figure 1:
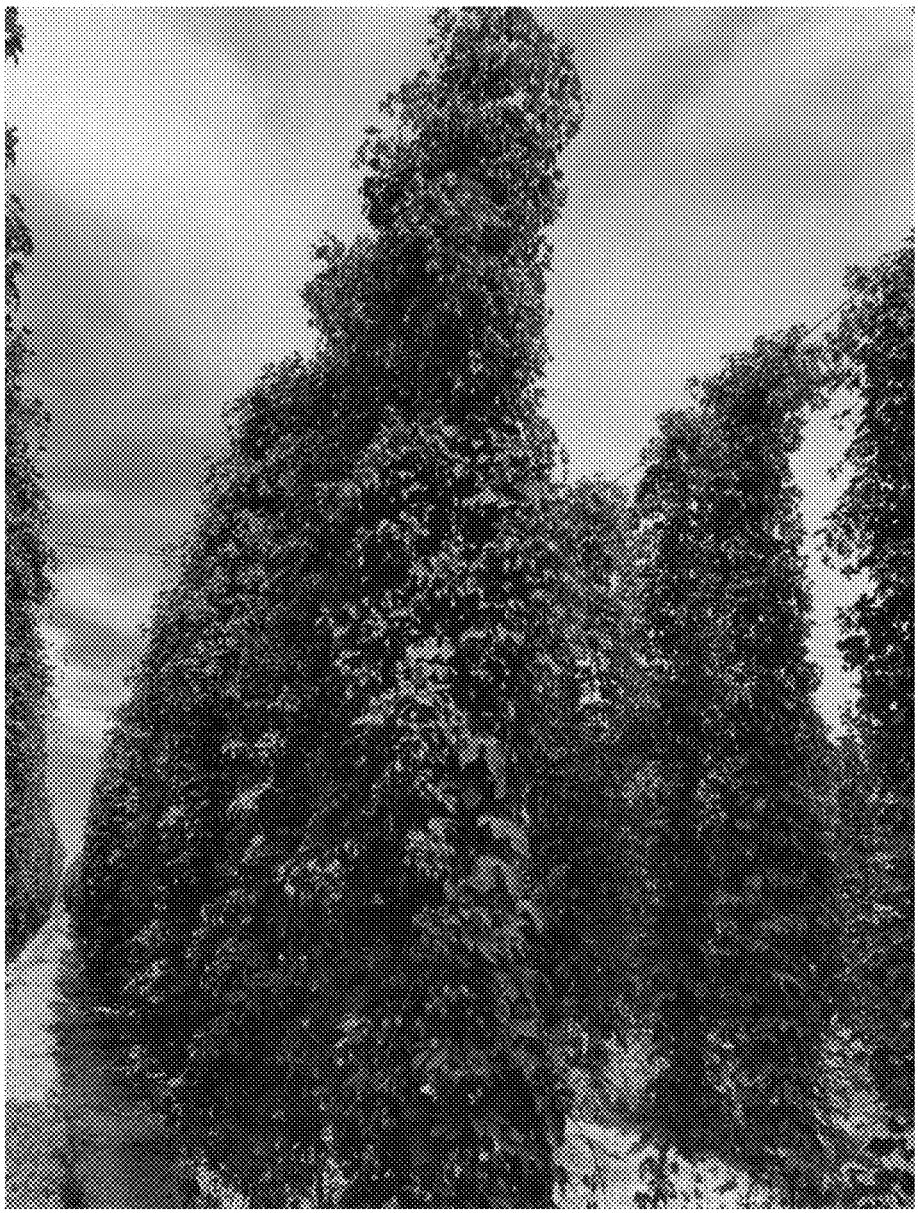
FIG. 1 illustrates a maturing 'HBC 1019' hop plant as growing on a trellis.
Figure 2:
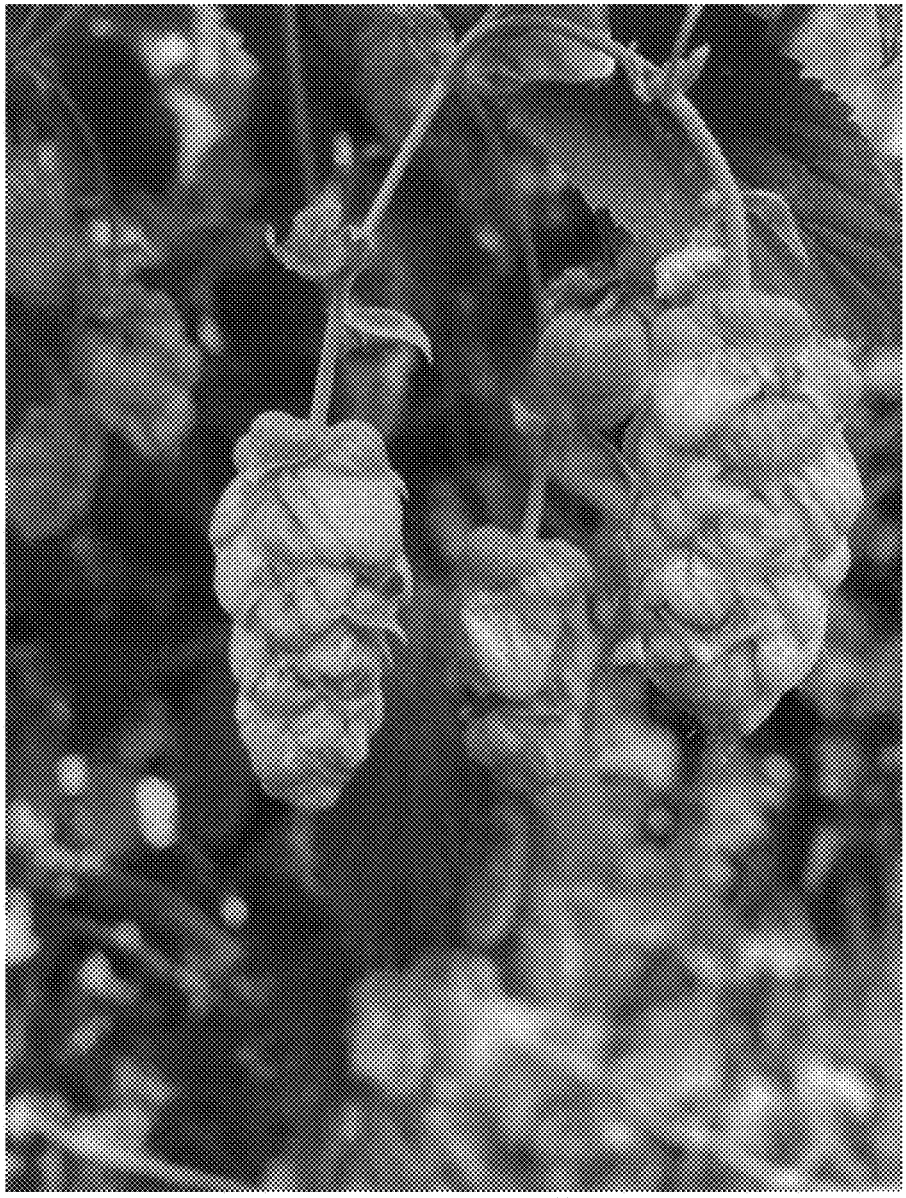
FIG. 2 illustrates whole mature cones of a 'HBC 1019' hop plant.
Figure 3:
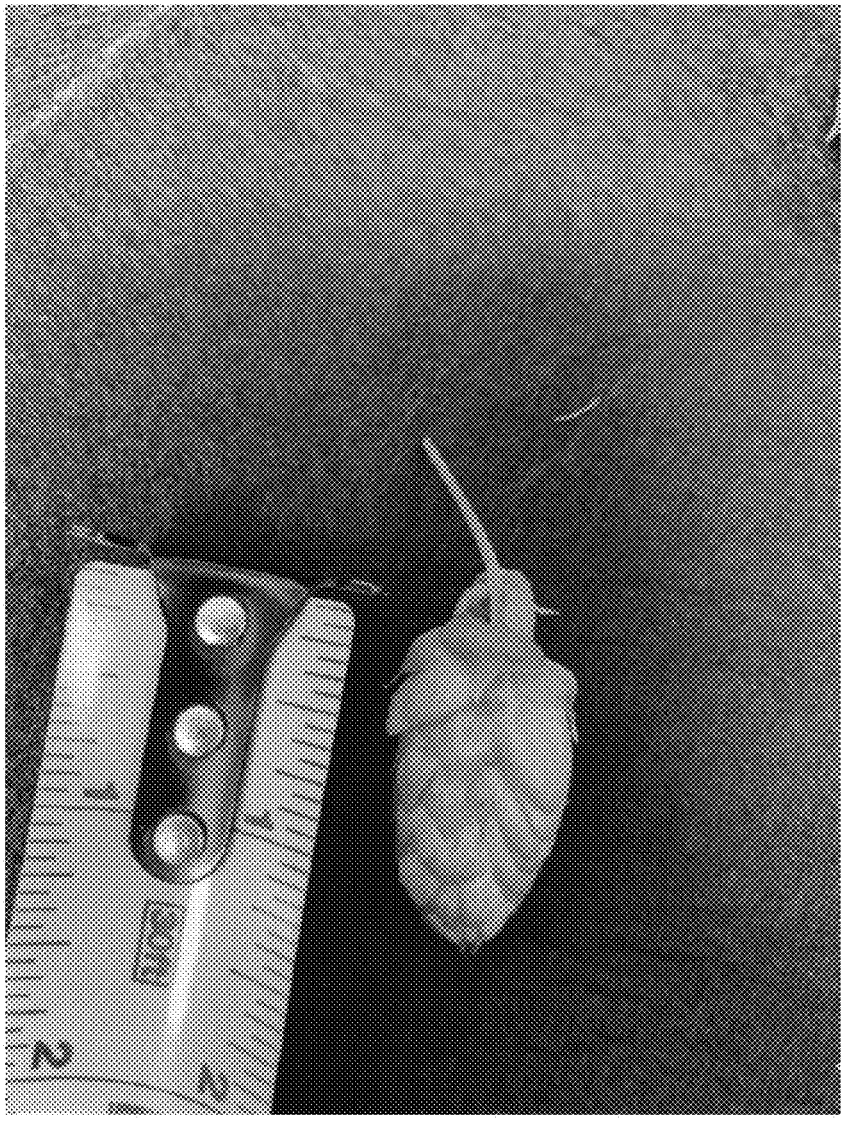
FIG. 3 illustrates a mature hop cone of a 'HBC 1019' hop plant.
Figure 4:
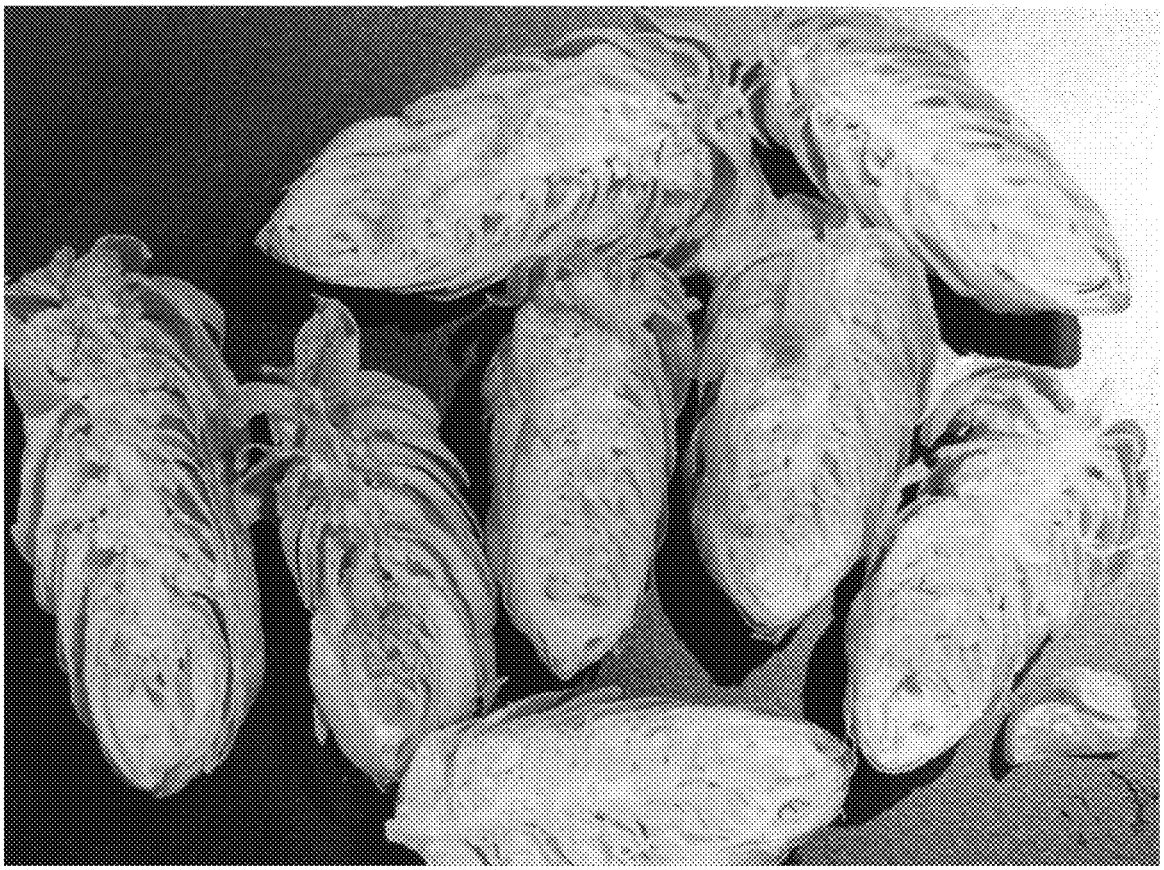
FIG. 4 illustrates cross sections of mature cones of a 'HBC 1019' hop plant.
Figure 5:
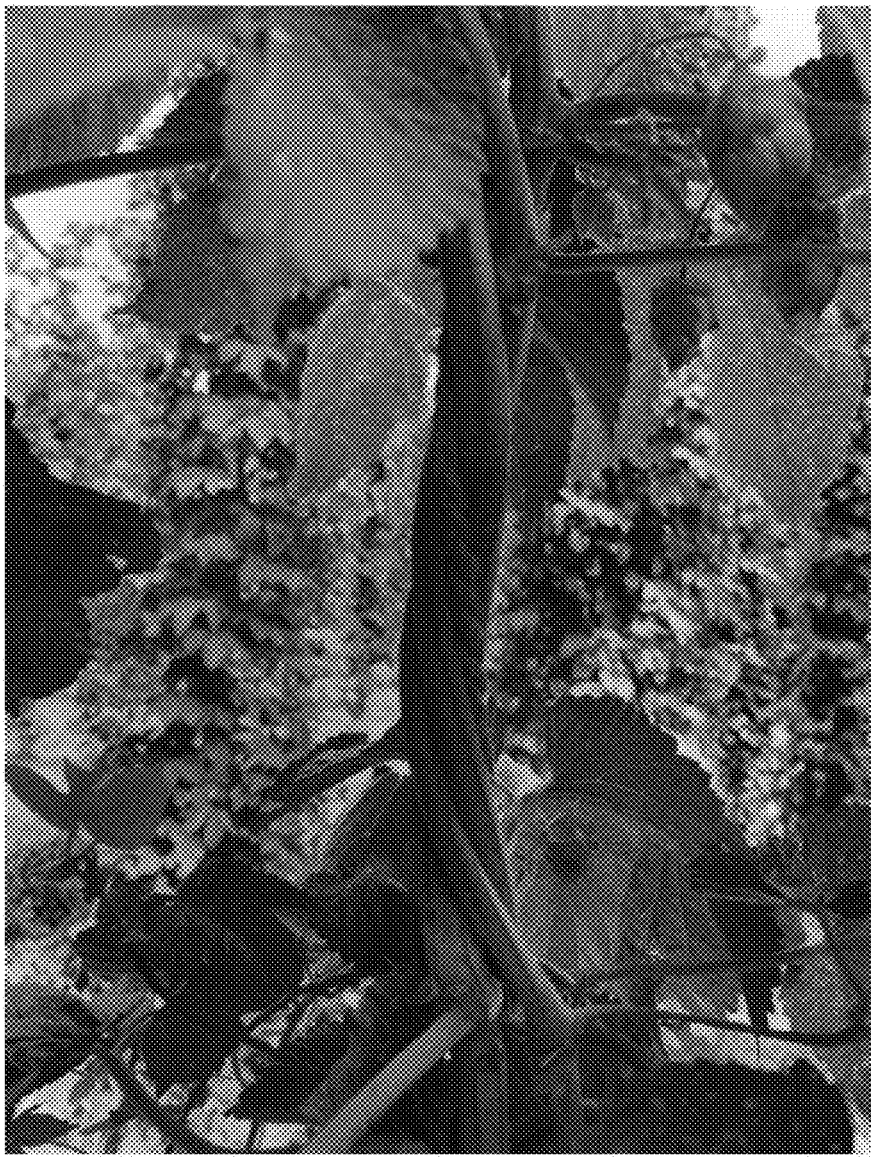
FIG. 5 illustrates mature bines and cones of a 'HBC 1019' hop plant.
Figure 6:
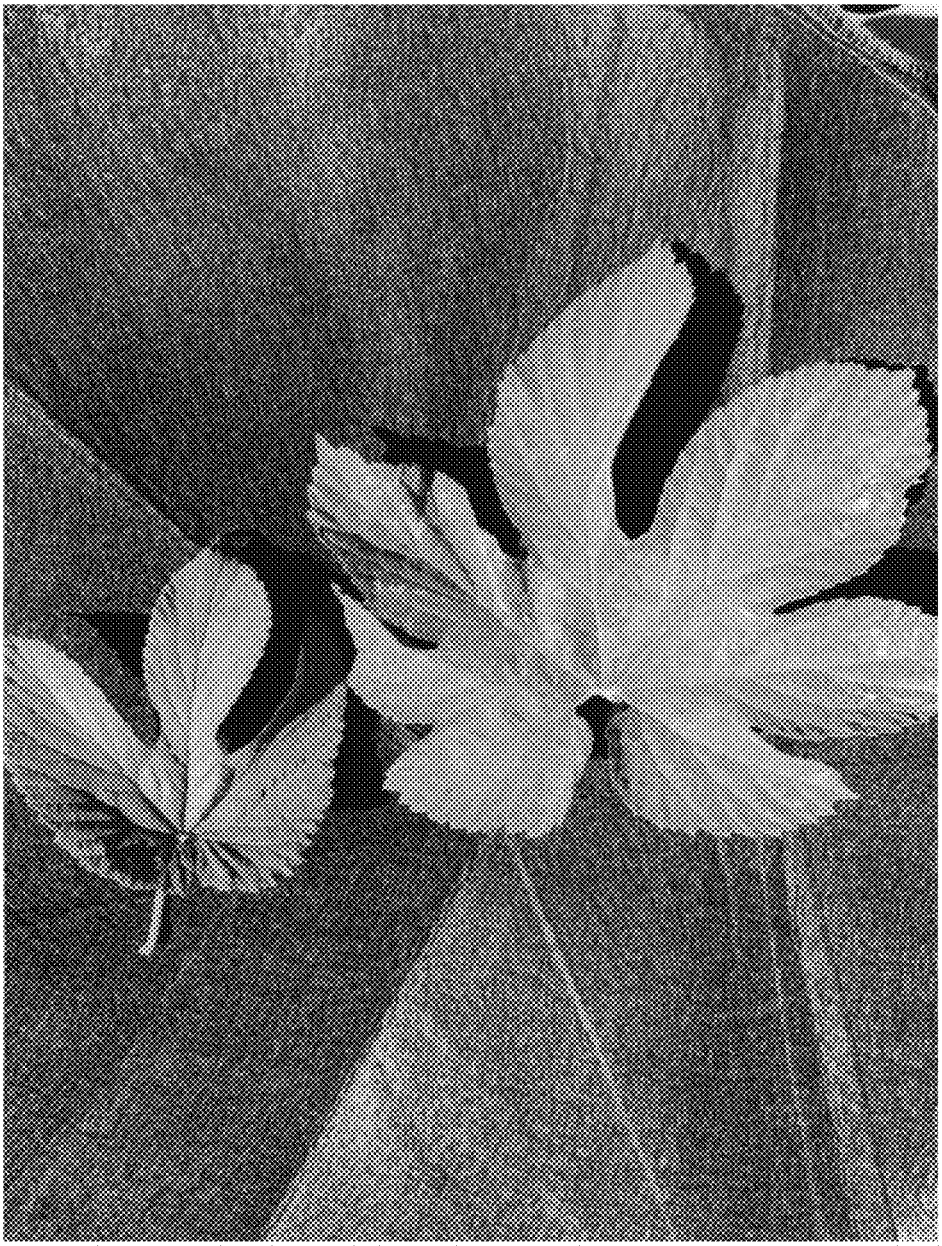
FIG. 6 illustrates leaves of a mature 'HBC 1019' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made late in the 2020 growing season at the test block of 'HBC 1019' plants near harvest maturity, under typical growing conditions near Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, published by The Royal Horticultural Society of Great Britain.

Ploidy: Diploid.

Sex: Female.

Use: Brewing beer and ale.

Plant shape: Climbing bine, columnar growth, on typically 17 ft to 18 ft trellis height.

Yield: Average yield is expected to be approx. 2,500 to 3,200 pounds per acre.

Oil analytical characteristics (averages):

| | |
|---|---|
| % Alpha Acid (% cone weight) | 11.4 |
| % Beta Acid (% cone weight) | 8.8 |
| % Cohumulone (% alpha acids) | 23 |
| Total Oils (ml/100 g of cones): | 1.8 |
| Hop Storage Index (% loss) | 27 |

Bine:

*Bine color*.—Yellow-Green 146D.
*Stripe present*.—Yes.
*Stripe color*.—Red-Purple 60C.
*Stipule direction*.—Intrapetiolar.
*Stipule color*.—Yellow-Green 145A.
*Average number of stipules per bine*.—58.
*Bine diameter*.—12 mm at base; 12 mm at nine feet; and 11 mm at terminal end of eighteen feet.
*Typical bine length*.—4.6 m.
*Typical internode length* (*bine*).—20 cm to 23 cm.
*Typical internode length* (*lateral*).—17 cm to 20 cm.
*Average lateral length* (*on bottom third of plant*).—130 cm.
*Average lateral length* (*on middle third of plant*).—132 cm.
*Average laterals length* (*on upper third of plant*).—126 cm.
*Lateral density* (*on middle third of plant*).—Medium (two laterals per node).

Leaf:

*Arrangement*.—Opposite.
*Shape*.—Palmately lobed.
*Apex*.—Caudate.
*Base*.—Cordate.
*Average length of mature leaf*.—14 cm.
*Average width of mature leaf*.—11 cm.
*Color of mature leaf upper surface*.—Green 139A.
*Color of mature leaf lower surface*.—Green 137A.
*Color of immature leaf upper surface*.—Green 137A.
*Color of immature leaf lower surface*.—Green 137A.
*Number of lobes*.—5.
*Margin*.—Serrate.
*Serrations per inch*.—3 (typically).
*Pose*.—Horizontal.
*Average petiole length* (*of mature leaf*).—5.7 cm.
*Average petiole diameter* (*of mature leaf*).—4.7 mm.
*Petiole color at base*.—Yellow-Green 146D.
*Venation*.—Palmate.
*Vein color*.—Yellow-Green 146C.

Cone:

*Avg. length*.—3 cm.
*Avg. diameter*.—16 mm.
*Typical cone weight*.—0.83 g.
*Cone shape*.—Cordate.
*Bract tip color*.—Yellow-Green 145A.
*Bract base color*.—Yellow-Green 145B.
*Bract shape*.—Ovate.
*Bract length*.—11 mm.
*Bract width*.—11 mm.
*Bract tip shape*.—Cuspidate.
*Bract tip position*.—Alternating.
*Bract base shape*.—Rounded.
*Bract margin*.—Entire.
*Degree of bract opening* (*closed, slightly open, clearly open*).—Slightly open.
*Bracteole color* (*lower surface*).—Yellow-Green 144D.
*Bracteole color* (*upper surface*).—Yellow-Green 144A.
*Bracteole shape*.—Ovate.
*Bracteole length*.—10 mm.
*Bracteole width*.—8.5 mm.
*Lupulin glands shape*.—Peduncutlated oblong polyps.
*Lupulin glands number per cone*.—Varies greatly — Moderate to many.
*Time of flowering*.—Mid to late July.

What is claimed:

1. A new and distinct variety of Hop plant named 'HBC 1019', substantially as illustrated and described herein.

* * * * *